United States Patent [19]

Kotani et al.

[11] 4,287,345
[45] Sep. 1, 1981

[54] POLYFUNCTIONAL DISULFIDE COMPOUNDS HAVING S—S EXCHANGE REACTIVITY

[75] Inventors: Kikuo Kotani; Kunio Ohyama; Nobuaki Nakagawa, all of Shizuoka; Tadashiro Fujii, Mishima; Susumu Watanabe, Shizuoka, all of Japan

[73] Assignee: Toyo Jozo Kabushiki Kaisha, Shizuoka, Japan

[21] Appl. No.: 111,482

[22] Filed: Jan. 11, 1980

[30] Foreign Application Priority Data

May 4, 1979 [JP] Japan .................................. 54-41737
Dec. 1, 1979 [JP] Japan .................................. 54-3507

[51] Int. Cl.³ .......................................... C07D 213/70
[52] U.S. Cl. .................... 546/261; 546/270; 435/7; 435/181
[58] Field of Search ............................... 546/270, 261

[56] References Cited

U.S. PATENT DOCUMENTS 4,049,665  9/1977  Douglass .............................. 546/261
4,053,606  10/1977  Shen et al. ........................... 546/261

FOREIGN PATENT DOCUMENTS 48-6467  2/1973  Japan ...................................... 546/261

OTHER PUBLICATIONS

Pharmacia Fine Chemicals, Dec. 1974, pp. 3-6.
Biochem. Journal, 1973, vol. 133, pp. 573-584 by Brooklehurst et al.

Primary Examiner—Henry R. Jiles
Assistant Examiner—Jane T. Fan
Attorney, Agent, or Firm—Young & Thompson

[57] ABSTRACT

A polyfunctional disulfide compound, useful as a cross-linking reagent having S—S exchange reactivity, of the formula

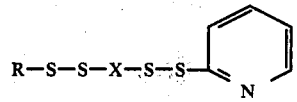

wherein R is 2-benzothiazolyl or 2-pyridyl-N-oxide and X is a spacer group having an alkylene group directly bonded to each S—S group.

4 Claims, No Drawings

POLYFUNCTIONAL DISULFIDE COMPOUNDS HAVING S—S EXCHANGE REACTIVITY

This invention relates to novel polyfunctional disulfide compounds of the formula

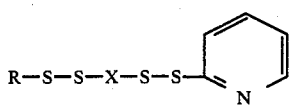

[I]

wherein R is 2-benzothiazolyl or 2-pyridyl-N-oxide, and X is a spacer group having an alkylene group directly bonded to each S- S group.

The novel polyfunctional disulfide compounds of formula [I] of the present invention (hereinafter called polyfunctional compounds [I]) are useful as cross-linking reagents having functional groups for S-S exchange reactivity of two different kinds.

The said polyfunctional compounds [I] show an S-S exchange reaction upon equimolar reaction with a compound having a thiol group, for example an enzyme, an immune related compound such as a hapten, antigen or receptor, a carrier such as a protein carrier or an immobilized carrier, or a thiol-modified derivative. At the first step of the reaction, the S-S group bound to 2-benzothiazolyl shows an S-S exchange reaction with the thiol group in a compound having a thiol group. After the said first step of the reaction, when further compound having a thiol group is added and subjected to reaction, then the S-S group bound to 2-pyridyl shows a second step of S-S exchange reactivity in which the S-S group bound to the 2-pyridyl group is reacted with its thiol group.

The polyfunctional compound [I] of the present invention can be used, based on its functional group activity, by optional selection and combination with a compound having a thiol group such as immune related compounds, carriers or their thiol-modified derivatives, for the preparation of a labelled substance for immunoassay, a combination of enzymes and immune-related compounds, immobilized enzymes, a combination of enzymes and insoluble carriers, a solid phase for immunoassay, a combination of immune-related substances and insoluble carriers, carriers for affinity chromatography, or haptenic combinations for antibody formation comprising haptens and protein carriers.

We have found that a polyfunctional compound [I] obtained by reaction with a carboxylic acid derivative of the formula

R—S—S—CH$_2$—CH$_2$—COOH     [II]

wherein R has the same meanings as hereinbefore, and an amine derivative of the formula

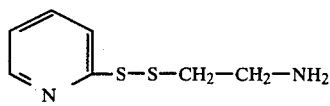

[III]

has stepwise S-S exchange reactivity, in which an S-S group bound to 2-benzothiazolyl or 2-pyridyl-N-oxide shows a first-order S-S exchange reaction for a compound having a thiol group, and another S-S group bound to 2-pyridyl shows a second-order S-S exchange reaction.

Further, two kinds of compounds having thiol groups can be reacted stepwise with compound [I]; and hence compound [I] is a useful compound for various reactions in which compounds having thiol groups are quantitatively bound to both ends of compound [I].

Another method for preparing the polyfunctional compound [I] is that 2,2'-dithio-bis-(benzothiazole) or 2,2'-dithio-bis-(pyridine) is reacted with a dithiol compound of the formula

HS—X—SH     [IV]

wherein X has the same meaning hereinbefore (hereinafter called dithiol compound [IV]), in an inert medium.

Polyfunctional compound [I] of the present invention can be obtained, for example, by reacting a functional derivative of a carboxylic acid derivative of formula [II] with an amine derivative of formula [III] in an inert medium, at an equimolar ratio, at −20° C. to 30° C. for 10 minutes to 5 hours. Examples of inert media are dimethylformamide, chloroform, benzene, ethyl acetate, methylenechloride, tetrahydrofuran or mixtures thereof. The product polyfunctional derivative [I] can be obtained by conventional separation, isolation or purification methods.

The above carboxylic acid derivative of formula [II] can be obtained for example according to the method described in Japanese Patent Application No. 53-85900. For example, 2,2'-dithio-bis-(benzothiazole) or 2,2'-dithio-bis-(pyridine-N-oxide) is reacted with 3-mercaptopropionic acid at an equimolar ratio or slightly excess ratio of 3-mercapto propionic acid, in benzene, chloroform, carbon tetrachloride, acetone, methanol or ethanol, at 10°–70° C. for ten minutes to five hours. Thereafter the carboxylic acid derivative of formula [II] can be obtained by a conventional isolation method such as cooling, concentration or vacuum drying. The said carboxylic acid derivative is changed to its activated ester by treating the said acid derivative with N-hydroxy succinimide or p-nitrophenol and dicyclohexylcarbodiimide in a solvent such as dimethylformamide, ethyl acetate, tetrahydrofuran or dioxane, or changed to its acid chloride by reacting with thionyl chloride as a reactive derivative of the carboxylic acid derivative of formula [II]. The said reactive derivative is subjected to a condensation reaction with an amine derivative of formula [III], or it can be reacted directly with said amine derivative by a condensation agent such as dicyclohexylcarbodiimide. Further examples of amine derivatives of formula [III] are described in The Journal of Organic Chemistry, 29, 1635 (1964), in which 2-mercaptoethylamine is oxidized by hydrogen peroxide to obtain 2-aminoethyl-2'-aminoethanthiol sulfonate, and the said compound is reacted with 2-mercapto pyridine to produce the said amine derivative. Also it can be obtained by reaction of 2,2'-dithio-bis-(pyridine) and 2-mercapto ethylamine.

The above methods are only illustrative and are not to be construed as limiting.

Another method for producing polyfunctional compound [I] is by reacting 2,2'-dithio-bis-(benzothiazole) or 2,2'-dithio-bis-(pyridine) with a dithiol compound [IV] in an inert medium as explained before. Examples of inert media are solvents which can dissolve 2,2'-dithio-bis-(benzothiazole), 2,2'-dithio-bis-(pyridine) and dithiol compound [IV], for example an alcohol such as methanol or ethanol, tetrahydrofuran, dioxane, ethyl ether, dimethylformamide, dimethylsulfoxide, acetone, benzene or mixtures thereof. Also, mixtures of the above organic solvents and water or a buffer solution can be mentioned.

An example of dithiol compound [IV] is a compound in which a group directly bound to its thiol group is an alkylene group. The said alkylene group can be a straight or branched chain, or it can be substituted with hydroxyl, amino, carboxyl or a protected derivative, or it can be linked by an ether group. Examples are $C_{2-10}$ dithiol compounds such as 1,2-dimercaptoethane, 1,4-dimercaptobutane, 1,6-dimercaptohexane, 1,8-dimercaptooctane, 1,9-dimercaptononane, 1,10-dimercaptodecane, 2,3-dimercapto-1-propanol, di(2=mercaptoethyl)-ether, dithioerythrytol or dithiothreitol.

The polyfunctional compound [I] has S-S groups at both sides of its spacer group, and a 2-benzothiazolyl group, a 2-pyridyl-N-oxide group or a 2-pyridyl group is bound to each S-S group. The said spacer group is identical with the group X in dithiol compound [IV], and is a group having an alkylene group directly bonded to each S-S group. The said alkylene group can be a straight or branched chain or may have hydroxy substituents, amide linkages or ether linkages. Examples are $C_{2-10}$ spacer groups.

S-S exchange reactivities of the polyfunctional compounds of the present invention are illustrated in Table 1.

In the Table, the compounds of formulae [Ia] and [Ib] hereinbeflow were used as the polyfunctional derivatives [I] of the present invention.

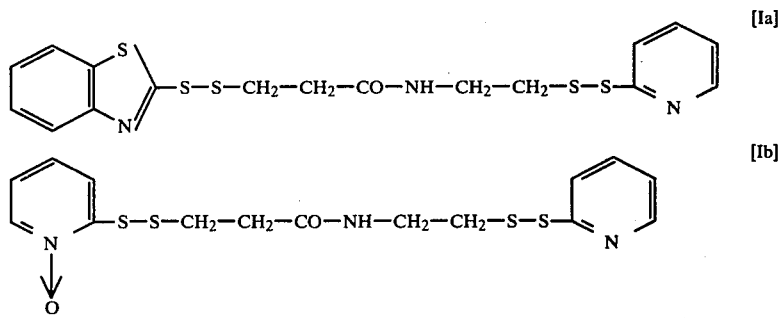

Dissolution of the 2,2'-dithio-bis-(benzothiazole), 2,2'-dithio-bis-(pyridine) and dithiol compound [IV] can be carried out previously or simultaneously. The ratio of each reagent is more than one mole or preferably 1-1.5 mole of 2,2'-dithio-bis-(benzothiazole) and more than one mole or preferably 5-30 moles of 2,2'-dithio-bis-(pyridine) per one mole of dithol compound [IV]. The reaction temperature is 0°-40° C. The reaction time may be varied according to the reaction temperature or solvent used and is usually 2-240 minutes. Isolation of the polyfunctional compound [I] can be carried out by conventional separation, isolation or purification methods such as solvent extraction or column chromatography.

Glutathione as a compound having a thiol group is used in its molar ratio of 0.5 to 2.0 times excess amount of the polyfunctional compounds in order to measure the S-S exchange reactivity of the compounds [Ia] and [Ib]. Its concentration is illustrated in the Table 1. The reaction was carried out in a 0.1 M phosphate buffer containing 1 mM of EDTA, at pH 7.2, as a reaction medium, at 25° C. for 30 minutes.

Maximum absorptions at 310 nm, 333 nm and 343 nm of thus-formed 2-mercaptobenzothiazole, 2-mercaptopyridine-N-oxide or 2-mercaptopyridine were measured at the concentration of 50 times dilution of the each reaction mixture.

TABLE 1

| Compound [I] [concentration] | amount added (molar ratio) [concentration] Glutathione added | | | |
|---|---|---|---|---|
| | 0.5 [$0.8 \times 10^{-3}$M/l.] | 1.0 [$1.6 \times 10^{-3}$m/l.] | 1.0 + 0.5 [$2.4 \times 10^{-}$M/l.] | 1.0 +1.0 [$3.2 \times 10^{-3}$M/l.] |
| [Ia] [$1.6 \times 10^{-3}$M/l.] | $\Delta A_{310}$ = 0.293 $\Delta A_{343}$ =0.002 *1 | $\Delta A_{310}$ = 0.601 $\Delta A_{343}$ 0.013 *2 | $\Delta A_{310}$ = 0.646 $\Delta A_{343}$ 0.127 *3 | $\Delta A_{310}$ = 0.693 $\Delta A_{343}$ = 0.249 *3 |
| [Ib] [$1.6 \times 10^{-3}$M/l.] | $\Delta A_{333}$ = 0.058 $\Delta A_{343}$ = 0.048 *4 | $\Delta A_{333}$ = 0.122 $\Delta A_{343}$ = 0.103 *5 | $\Delta A_{333}$ = 0.228 $\Delta A_{343}$ = 0.221 *6 | $\Delta A_{333}$ = 0.337 $\Delta A_{343}$ = 0.343 *6 |

TABLE 1-continued

| Compound [I] [concentration] | amount added (molar ratio) [concentration] Glutathione added | | | |
|---|---|---|---|---|
| | 0.5 [0.8 × 10⁻³M/l.] | 1.0 [1.6 × 10⁻³m/l.] | 1.0 + 0.5 [2.4 × 10⁻³M/l.] | 1.0 +1.0 [3.2 × 10⁻³M/l.] |
| Remarks | (I) | (II) | (III) | (IV) |

Explanation of Table 1:
*1 only absorption of 2-mercaptobenzothiazole was observed.
*2 absorption of about 3% of 2-mercaptopyridine was observed.
*3 after adding one mole of alutathione, strong absorption of 2-mercaptopyridine was observed, and no absorption change of 2-mercaptobenzothiazole was observed.
*4 only absorption of 2-mercaptopyridine-N-oxide was observed.
*5 absorption of about 1.4% of 1-mercaptopyridine was observed.
*6 aftyer adding one mole of glutathione, strong absorption of 2-mercaptopyridine was observed, and no absorption change of 2-mercaptopyridine-N-oxide was observed.

Remarks:
(I) S-S exchange reaction in which almost all glutathione was reacted with S-S group bound to 2-benzothiazolyl or 2-pyridyl-N-oxide group. High yield of reactivity was observed.
(II) Almost quantitative S-S exchange reaction for S-S group bound to 2-benzothiazolyl or 2-pyridyl-N-oxide was observed except S-S exchange reaction of several percent of glutathione for an S-S group bound to a 2-pyridyl group was obsered.
(III) Adding up to one mole of glutathione, the S-S exchange reaction for an S-S group bound to 2-benzothiazolyl or to 2-pyridyl-N-oxide proceeded. Further addition of glutathione carried out the reaction stepwise with the remaining S-S groups bound to 2-pyridyl groups.
(IV) Same as above (III).

When an excess amount of glutathione was used, the reaction was performed at first by adding an equimolar ratio of glutathione and after confirmation of the reaction product, then the remaining excess amount of glutathione was added.

ΔA in the table shows the difference of the absorbency at each maximum absorption wave length before and after the reaction.

The molar absorption coefficient at maximum absorption wave length is as follows:

2-mercaptopyridine-N-oxide: 3830 (333 nm), 3190 (343 nm).

2-mercaptobenzothiazole: 19300 (310 nm), 160 (343 nm).

2-mercaptopyridine: 3170 (310 nm), 7270 (333 nm), 8130 (343 nm).

As shown in Table 1, the polyfunctional compound [I] of the present invention is a novel compound having S-S exchange reactivity which shows two stepwise reactivities for a compound having a thiol group. Further the said S-S exchange reactivity is constant for direction of reaction and is quantitative.

Another S-S exchange reactivity can be observed when, for example, the polyfunctional compound [I] is dissolved in 0.1 M phosphate buffer (pH 7.5) containing 10% dimethylformamide, and 2-mercaptoethanol was added. The amounts of produced 2-mercaptobenzothiazole and 2-mercaptopyridine were analyzed, thereby confirming the S-S exchange reactivity of the compound.

The polyfunctional compound [I] of the present invention has various uses, for example, as a cross-linking reagent for the bound complex of enzyme and hapten, antigen, antibody or receptor in enzyme immune assay and enzyme receptor assay; a cross-linking reagent for the bound complex of hapten and enzyme for antigen formation; an immobilizing reagent for immobilization of solid carrier and hapten, antigen, antibody or receptor in immuno-assay; an immobilizing reagent for the bound complex of enzyme and carrier in immobilized enzyme; or immobilizing reagent for hapten, antigen, antibody or receptor and carrier in affinity chromatography. Also reactive derivatives of the above physiologically active substances or carriers having S-S exchange reactivity can be obtained by reacting those substances or carrier and the polyfunctional compound.

The compounds of the present invention can be obtained by reacting an inert solvnt such as water, phosphate buffer, dimethylformamide, tetrahydrofuran or mixtures thereof, at ambient temperature for 10 minutes to 24 hours.

Also the above-mentioned physiologically active substances or carriers are not limited to compounds having thiol groups, for example enzymes such as β-galactosidase and urease, or commercially available carriers having thiol groups such as acrylamide polythiol or glass compounds having thiol groups. Physiologically active substances or carriers such as proteins or peptides having S-S groups in their molecular structure can be used after reduction of the said S-S group. Thiol groups can be introduced into functional groups such as amino groups, for example by using S-acetyl-mercaptosuccinic anhydride [Arch. Biochem. Biophys., 96, 605–612 (1962)]. Also the functional derivatives of disulfide derivatives having 2-benzothiazolyl or 2-pyridyl-N-oxide groups can be reacted with amino groups in a physiologically active substance or carrier (Japanese Patent Appln. No. 53-85900) and the said S-S groups are cleaved by treating with dithiothreitol or alkali such as an aqueous medium having a pH above 9.5 to introduce thiol groups.

The following examples illustrate the present invention but are not to be construed as limiting:

EXAMPLE 1

(1) To 2,2'-dithio-bis-(benzothiazole) (40 g) was added benzene (1.5 lit.) and 3-mercaptopropionate (8.0 g), and the mixture was reacted at 70° C. for three hours with stirring. Thereafter the reaction mixture was cooled to room temperature, concentrated in vacuo and allowed to stand overnight at 5° C., to precipitate the crude crystals which are recrystallized from benzene to obtain 3-(2'-benzothiazolyl-dithio) propionate crystals (16.25 g).

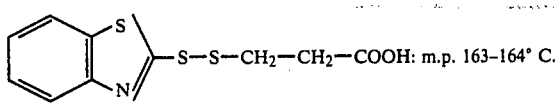

S—S—CH₂—CH₂—COOH: m.p. 163-164° C.

To 3-(2'-benzothiazolyl-dithio)-propionate (8.13 g) in dimethylformamide (80 ml) were added N-hydroxysuccinimide (34.5 g) and dicyclohexylcarbodiimide (6.8 g), and the mixture was stirred under ice cooling for one hour and at ambient temperature for two hours. The precipitated dicyclohexylurea was filtered off and the filtrate was added to 10 volumes of water and the precipitate formed was filtered, dried, and repeatedly recrystallized from benzene to obtain crystals of 3-(2'-benzothiazolyl-dithio)propionate N-succinimide ester (7.18 g).

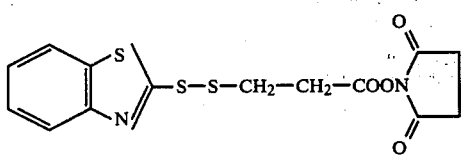

m.p. 122-123° C.

λmax=270 nm [dimethylformamide:phosphate buffer (0.1 M, ph 7.5)=1:5]

Rf=0.53 (silica gel TLC, benzene:ethyl acetate=3:1)

(2) To 2-mercapto ethylamine hydrochloride (10.0 g) dissolved in water (40 ml) was dropwise added 30% aqueous hydrogen peroxide (4.5 ml) with stirring under cooling for 30 minutes. 30% aqueous hydrogen peroxide (9.0 ml) was added and the mixture was allowed to stand at room temperature for 24 hours. The reaction mixture was concentrated in vacuo to obtain a syrup, and anhydrous ethanol was added thereto to obtain crude crystals (10.7 g) which were recrystallized by glatial acetic acid to yield 2-aminoethyl-2'-aminoethane thiolsulfonate-2 hydrochloride as white needle-like crystals (9.77 g).

[H₂N—CH₂—CH₂SO₂—S—CH₂—CH₂—NH₂.2HCl: m.p. 165°-166° C.]

To the 2-aminoethyl-2'-aminoethane thiosulfonate.2HCl (7.7 g) dissolved in aqueous solution (12 ml) containing 3 ml of concentrated hydrochloric acid was added dropwise an ethanol solution (12 ml) of 2-mercaptopyridine (3.33 g) with stirring at room temperature. After stirring for 20 hours, ethanol was distilled off from the reaction mixture under reduced pressure, and chloroform was added thereto, to extract the unreacted substance. A cooled aqueous solution containing potassium hydroxide (8.4 g) was added and the reaction mixture was extracted with chloroform, and twice more extracted with chloroform. These extracts were immediately shaken with conc. HCl. The conc. HCl layer was combined and concentrated to obtain a syrupy substance. Anhydrous ethanol was added thereto to precipitate crude crystals (4.91 g) which were recrystallized from anhydrous ethanol to yield 2-pyridyl-2'-aminoethyl disulfide.2 HCl (3.68 g).

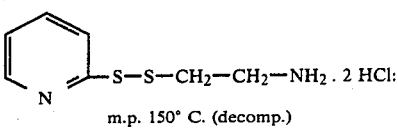

S—S—CH₂—CH₂—NH₂ . 2 HCl:
m.p. 150° C. (decomp.)

(3) 2-pyridyl-2'-aminoethyl disulfide.2 HCL (2.0 g) was dissolved in water (20 g). After adjusting the solution to pH 10 by adding 1 N aqueous potassium hydroxide, the mixture was extracted with ethyl acetate. The ethyl acetate layer was washed with water and dried with anhydrous sodium sulfate. To the ethyl acetate layer was added dropwise an ethyl acetate solution of 3-(2'-benzothiazolyl-dithio) propionate-N-succinimide ester (2.27 g) under cooling with stirring; and the mixture was reacted for 90 minutes, and the precipitate formed was filtered and dried. The dried residue was dissolved in chloroform, washed with 5% aqueous sodium hydrogen carbonate under ice-cooling, washed with water, dried with anhydrous sodium sulfate and the chloroform layer was concentrated. Hexane was added to the concentrate to obtain N-[2-(2'-pyridyl-dithio) ethyl]-3-(2'-benzothiazolyl-dithio)-propionamide (2.07 g)

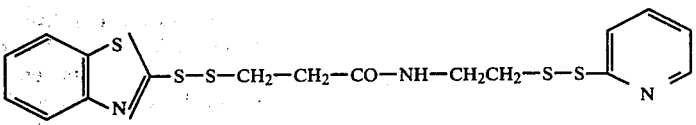

λmax=282 nm,
$E_1\ {}_{cm}^{1\%}=235$ [dimethylformamide:0.1 M phosphate buffer (pH 7.5)=1:9]

Rf=0.41 (chloroform:ethylacetate=1:1, silica gel TLC)

Rf=0.12 (benzene:ethyl acetate=3:1, silica gel TLC)

The reactivity and utility of this compound can be clearly understood from the following:

To 0.15 M (0.85%) NaCl containing anti-insulin antibody-Fab' (2.0 mg) and phosphate buffer containing 1 mM EDTA (hereinafter called PBS) (0.01 M, ph 7.2) (2.0 ml) was added 10% dimethylformamide solution of PBS (0.01 M, pH 7.2) containing a 50 mcg/ml solution of N-[2-(2'-pyridyl-dithio) ethyl]-3-(2'-benzothiazolyl-dithio) propionamide (365 μl) and the mixture was reacted at 25° C. for 30 minutes. Absorptions at 310 nm and 343 nm of the reaction mixture were measured. 96% of 2-mercaptobenzothiazole and 3% of 2-mercaptopyridine in N-[2-(2'-pyridyl-dithio) ethyl]-3-(2'-benzothiazolyl-dithio) propionamide in the reaction mixture were detected.

To another sample of this reaction mixture was added 2-mercaptoethanol. No increase of absorption of 2-mercaptobenzothiazole was observed; however the absorption of 2-mercaptopyridine was observed and 93% was formed.

As a result, about 96% of anti-insulin antibody-Fab' was reacted by S-S exchange reaction with the S-S group bound to the 2-benzothiazolyl group.

After adjusting the reaction mixture (0.5 ml) with 0.1 N aqueous NaOH at pH 8.5, a solution of β-galactosidase (4.37 mg) dissolved in PBS (0.01 M, pH 8.5) was incubated at 25° C. for one hour. Gel-filtration [developer: PBS (0.01 M, pH 7.2)] using a Sephadex G-50 (tradename, Pharmacia Finechemicals Co.) column (1.5×84 cm) was carried out and fractions Nos. 11–13, each 5.0 ml, were collected. These fractions contained 4.6% of unreacted β-galactosidase and unreacted anti-insulin antibody-Fab' was not detected.

From these results, in this elution, anti-insulin antibody-Fab' was bound at a ratio of 1:1 for β-galactosidase. The SH group of anti-insulin antibody-Fab' was reacted by an S-S exchange reaction with the S-S group bound to the 2-benzothiazolyl group, and the SH group of β-galactosidase was reacted for S-S exchange reaction with the S-S ground bound to the 2-pyridyl group.

The above anti-insulin antibody-Fab' was prepared as follows: To IgG containing anti-insulin antibody (50 mg) dissolved in 0.1 M acetate buffer (pH 4.5, 2 ml) was added pepsin (1 mg, Sigma Co.), and the mixture was incubated at 37° C. for 16 hours. The solution was subjected to gel-filtration using a Sephadex G-150 (tradename) column [1.5×50 cm, developer: 0.1 M borate buffer (pH 8.0)] to obtain the active fraction containing F(ab')₂. The fraction was concentrated with a collodion pack, and dialysed against 0.1 M acetate buffer solution (pH 5.0) at 4° C. overnight. To the solution was added mercaptoethanolamine at 10 mM concentration and the mixture was incubated at 37° C. for 90 minutes. The reaction mixture was subjected to gel-filtration using a Sephadex G-25 (tradename) column [1.5×50 cm, developer: 0.1 M acetate buffer (pH 5.0)] and there was obtained the Fab' fraction (15 mg). The concentration of SH group per one mole of the thus-obtained anti-insulin antibody-Fab' was about 0.95 mole. [J. Immunol., 116 (6), 1554 (1976)].

EXAMPLE 2

2,2'-dithio-bis-(pyridine-N-oxide) (5.05 g) was dissolved in chloroform (200 ml) and there was added dropwise 3-mercaptopropionate (2.55 g) and the mixture was reacted at 40° C. for one hour. The reaction mixture was cooled, and the crude crystals precipitated and were recrystallized from chloroform to obtain crystals of 3-(2'-pyridyl-N-oxide-dithio) propionate (3.72 g) [Rf: 0.63 (TLC, silica gel, n-butanol-acetic acid:water=4:1:1)].

2-pyridyl-2'-aminoethyl disulfide.2 HCl (20 g) obtained by the same process as in Example 1 was dissolved in water (20 ml), adjusted to pH 10 under ice-cooling by addition of aqueous NaOH, extracted with chloroform and the chloroform layer was collected, washed with water, dried with anhydrous sodium sulfate then concentrated in vacuo.

To the above 3-(2'-pyridyl-N-oxide-dithio) propionate (1.19 g) dissolved in tetrahydrofuran (50 ml) was added dropwise tetrahydrofuran solution (2 ml) of dicyclohexylcarbodiimide (1.06 g) under cooling with stirring. After 20 minutes, this solution and the above concentrated solution were mixed with stirring under ice-cooling for one hour and at room temperature for three hours.

Precipitated dicyclohexylurea was removed by filtration and to the filtrate was added water and the mixture was extracted with chloroform. The chloroform layer was washed with 5% HCl, 5% aqueous sodium hydrogen carbonate and water, dried with anhydrous sodium sulfate and the chloroform was distilled off to obtain N-[2-(2'-pyridyl-dithio) ethyl]-3-(2'-pyridyl-N-oxide-dithio) propionamide.

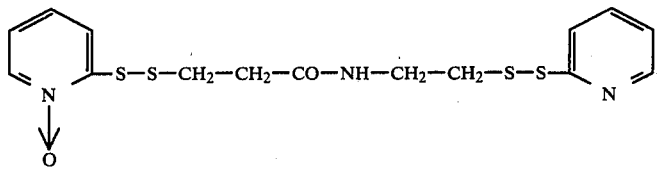

Rf=0.55 (upper layer of n-butanol:pyridine:acetic acid:water=10:3:0.1:11; silica gel TLC)

EXAMPLE 3

To 2,2'-dithio-bis-(benzothiazole) (20 mg) dissolved in 0.1 M phosphate buffer (pH 6.4, containing 1 mM EDTA) (3 lit.) containing 40% ethanol was added dropwise 2,2'-dithio-bis-(pyridine) (397 mg) dissolved in 0.1 M phosphate buffer (pH 6.4, containing 1 mM EDTA) (1 lit.) containing 40% ethanol and 1,2-dimercaptoethane (5.7 mg) dissolved in the same buffer solution mixture (1 lit.) with stirring for 60 minutes. After reaction, ethanol was distilled off, the mixture was extracted three times with chloroform, the chloroform layer was collected, dried with anhydrous sodium sulfate and concentrated. The concentrate was charged on a solumn of silica gel (1.0×40 cm), and eluted with benzene:ethyl acetate (20:1). The active fractions were collected and dried in vacuo to yield 1-(2'-benzothiazolyl-dithio)-2-(2'-pyridyl-dithio) ethane (13.2 mg).

Physico-chemical properties are as follows:
λmax=279 nm [dimethylformamide: 0.1 M phosphate buffer (pH 7.5)=1:9]
Rf+0.51 (silica gel TLC, benzene:ethyl acetate=10:1)

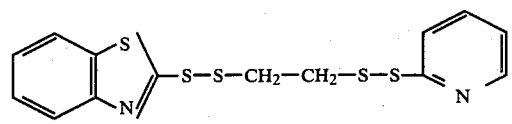

To 0.1 M phosphate buffer (pH 7.5) containing 0.030 mM of this compound dissolved in 10% dimethylformamide was added 2-mercaptoethanol at 0.1% concentration. 2-mercaptobenzothiazole (0.029 mM) and 2-mercaptopyridine (0.028 mM) were liberated.

EXAMPLE 4

To a mixed solution of 2,2'-dithio-bis-(benzothiazole) (20 mg) dissolved in 0.1 M phosphate buffer (pH 6.4, containing 1 mM EDTA) (3 lit.) containing 40% ethanol and 2,2'-dithio-bis-(pyridine) (132 mg) dissolved in the same buffer solution (1 lit.) was added dropwise 1, 10-dimercaptodecane (12.4 mg) dissolved in the same buffer solution (1 lit.) at room temperature with stirring and reacted for 90 minutes.

After reaction, ethanol was distilled in vacuo, and the mixture was extracted three times with chloroform. The chloroform layer was collected, dried with anhydrous sodium sulfate and concentrated. The concentrate was charged on a column of silica gel (1.0×20 cm), eluted with benzene:ethyl acetate (20:1), and the active fractions were collected and dried in vacuo to obtain 1-(2'-benzothiazolyl-dithio)-10-(2'-pyridyl-dithio)-decane (19.5 mg).

Physico-chemical properties of this substance are as follows:

λmax=279 nm [dimethylformamide: 0.1 M phosphate buffer (pH 7.5)=1:9]
Rf=0.51 (benzene:ethyl acetate=10:1, silica gel TLC)
Rf=0.75 (benzene:ethyl acetate=3:1, silica gel TLC)

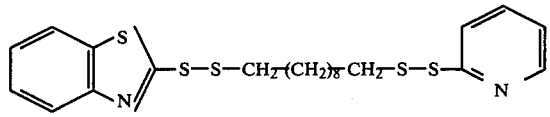

To a solution of this substance (0.030 mM) in 0.1 M phosphate buffer (pH 7.5) containing 10% dimethylformamide was added 2-mercaptoethanol at 0.1% concentration. 2-mercaptobenzothiazole (0.029 mM) and 2-mercaptopyridine (0.029 mM) were liberated.

EXAMPLES 5–12

2,2'-dithio-bis-(benzothiazole) and 2'-dithio-bis-(pyridine) and the following dithiol compounds [IV] were used, and the process was conducted as in Example 3 to obtain each corresponding polyfunctional compound [I].

Dithiol compounds [IV] used are as follows:

1,4-dimercaptobutane, 1,6-dimercaptohexane, 1,8-dimercaptooctane, 1,9-dimercaptononane, di(2-mercapto-ethyl)-ether, dithioerythritol and dithiothreitol.

The above polyfunctional compounds [I] in 0.1 M phosphate buffer solution (pH 7.5) containing 10% dimethylformamide liberated 2-mercaptobenzothiazole and 2-mercaptopyridine corresponding to 97–93% of the molar amount of the polyfunctional compound [I] by addition of 2-mercaptoethanol.

TABLE 2

| dithiol compound [II] and its amount used (mMole) | 2,2'-dithio-bis-(benzothiazole) amount used (mMole) | 2,2'-dithio-bis-(pyridine) amount used (mMole) | polyfunctional compound [I] Structure | yield (mg) | λmax* | Rf** |
|---|---|---|---|---|---|---|
| 1,4-dimercaptobutane 0.06 | 0.06 | 1.80 | Bt–S–S–CH$_2$–(CH$_2$)$_2$–CH$_2$–S–S–Py | 14.5 | 279 nm | 0.51 |
| 1,6-dimercaptohexane 0.06 | 0.06 | 0.60 | Bt–S–S–CH$_2$–(CH$_2$)$_4$–CH$_2$–S–S–Py | 16.2 | 279 nm | 0.51 |
| 1,8-dimercaptooctane 0.06 | 0.06 | 0.60 | Bt–S–S–CH$_2$–(CH$_2$)$_6$–CH$_2$–S–S–Py | 17.5 | 279 nm | 0.54 |
| 1,9-dimercaptononane 0.06 | 0.06 | 0.60 | Bt–S–S–CH$_2$–(CH$_2$)$_7$–CH$_2$–S–S–Py | 18.6 | 279 nm | 0.58 |
| di-(2-mercaptoethyl) ether 0.06 | 0.06 | 0.60 | Bt–S–S–CH$_2$–CH$_2$–O–CH$_2$CH$_2$–S–S–Py | 15.8 | 279 nm | 0.50 |
| dithioerythritol 0.06 | 0.06 | 0.60 | Bt–S–S–CH$_2$CH(OH)–CH(OH)–CH$_2$–S–S–Py | 16.0 | 279 nm | 0.52 |
| dithiothreitol 0.06 | 0.06 | 0.60 | Bt–S–S–CH$_2$CH(OH)–CH(OH)–CH$_2$–S–S–Py | 15.8 | 279 nm | 0.53 |

What is claimed is:

1. A polyfunctional disulfide compound of the formula

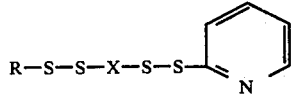

[I]

wherein R is 2-benzothiazolyl or 2-pyridyl-N-oxide and X is a C$_{2-10}$ spacer group which may have hydroxy substituents, amide linkage or ether linkage having an alkylene group directly bonded to each S-S group.

2. A compound as claimed in claim 1, wherein X is a spacer group having amide bond.

3. The compound claimed in claim 1, wherein X is a spacer group having an ether bond.

4. A compound as claimed in claim 1, wherein X is a member selected from the group consisting of:

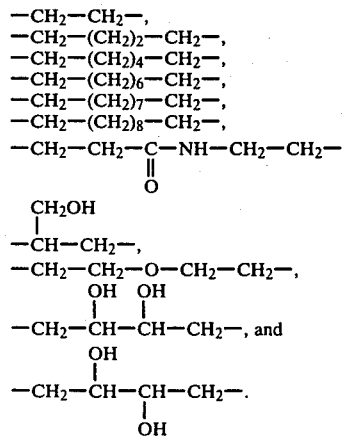

* * * * *